May 27, 1952 H. C. SWIM Plant Pat. 1,100
NECTARINE PLANT
Filed Feb. 20, 1951
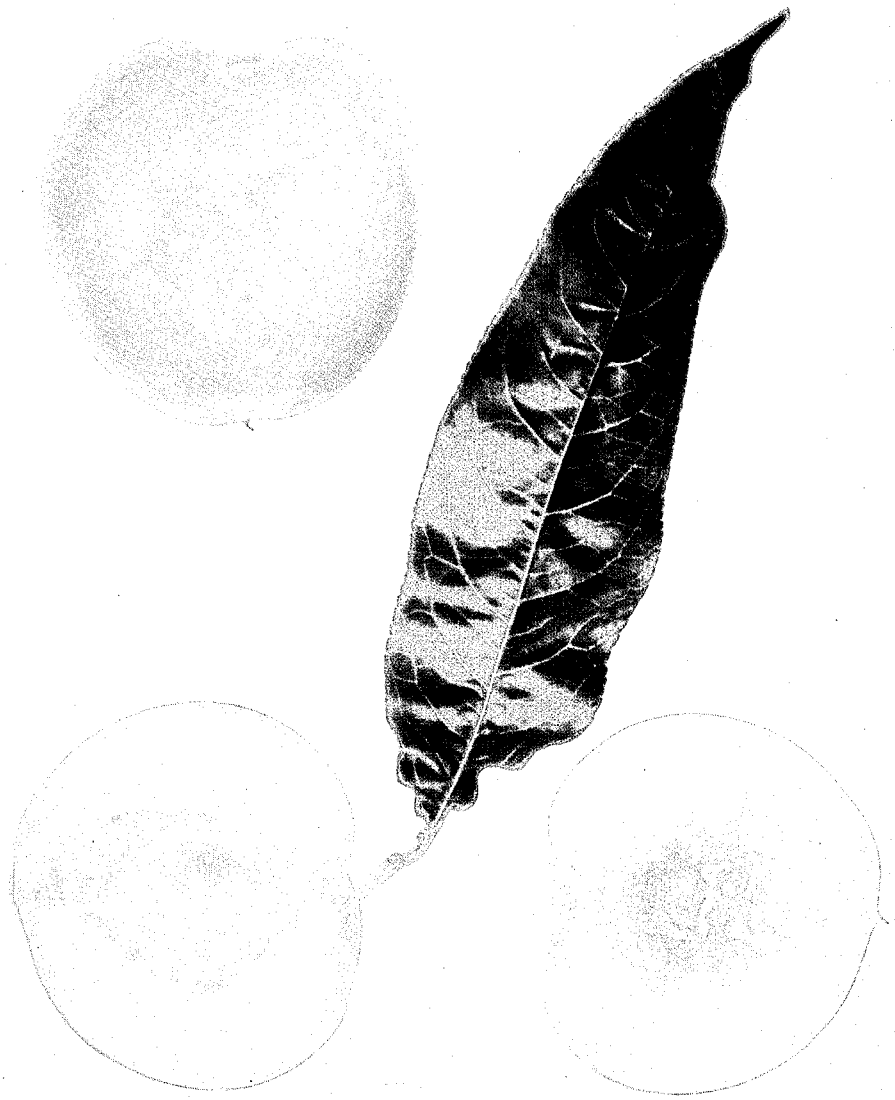
Inventor.
H. C. Swim
By: Robbs & Robb
Attorneys.

Patented May 27, 1952

Plant Pat. 1,100

UNITED STATES PATENT OFFICE 1,100

NECTARINE PLANT

Herbert C. Swim, Ontario, Calif., assignor to Armstrong Nurseries, Inc., Ontario, Calif., a corporation of California Application February 20, 1951, Serial No. 211,889

1 Claim. (Cl. 47—62)

The present invention relates to a new and distinct variety of nectarine plant, originated from seed resulting from hand-pollination of a first-generation seedling of "Babcock Peach" × "Boston Nectarine" (both unpatented) with pollen from a first-generation seedling of "Goldmine Nectarine" (unpatented) × "Rio Oso Gem Peach" (Plant Patent No. 84).

The aforementioned breeding has produced a materially improved variety of nectarine plant of the yellow-fleshed, freestone type having characteristics that are unlike any other known variety of nectarine in commerce today. The unique combination of improved characteristics of this new variety makes it stand out from all others, as well as from its parents. It most nearly resembles the variety "Pioneer" (Plant Patent No. 787), but differs essentially from this variety in the following important respects when grown under the same cultural conditions:

(1) The new variety has a shorter winter chilling requirement, making it more suited to areas having milder winters than is "Pioneer";

(2) The new variety usually ripens from one to two weeks earlier than "Pioneer," that is, between July 10 and July 25, as compared with July 17 to July 30 for "Pioneer";

(3) While the variety "Pioneer" is classified as a medium to vigorous grower, the new variety is characterized by its very vigorous habit of growth, producing larger and more obconic trees, and its lateral growths are longer, more upright, and slender;

(4) The fruit of the new variety is characterized by having more orange color in the skin and is somewhat less acid than "Pioneer."

Asexual reproduction of the new variety by budding at Ontario, California, shows that the foregoing characteristics come true to form and are established and transmitted through succeeding propagations.

In the drawing, there are illustrated specimens of this new nectarine tree foliage and fruit, the latter being shown in elevation, and also in section both with and without the stone or pit.

The following is a detailed description of the new variety, based upon observations of specimens grown at Ontario, California, with color terminology in accordance with Robert F. Wilson's Horticultural Colour Chart, except where noted as Ridgway's Color Standards and Nomenclature or where general color terms of ordinary dictionary significance are obvious:

Dates of first and last picking—Vary somewhat from year to year because of variable winter chilling in Southern California, but usually ripens the third week of July; picking period about 10 days.

Tree: Large; very vigorous; upright; spreading; more or less dense; obconic in shape; productive; regular bearer.

*Trunk.*—Stocky; medium shaggy.

*Branches.*—Medium stocky; moderately smooth; glossy. Color—color of one year old branch (1 cm. in diameter), bark is basically Argus Brown, Plate III (Ridgway) on side exposed to the sun with occasional darker markings of Warm Sepia, Plate XXIX (Ridgway), over the basic color. Portions of branch least exposed to the sun are near Courge Green, Plate XVII (Ridgway). Lenticels—medium in number; medium in size.

*Mature leaves.*—Blade length—13 to 16 cm.; width 3 to 4¾ cm.; large in size; acuminate; lanceolate; moderately thick. Leaf color—mature upper surface: near Parsley Green, Plate 00962, page 193; lower surface: near Courge Green, Plate XVII (Ridgway). Leaf conformation—usually somewhat undulant and crinkled along the midrib; sometimes smooth, however. Margin—glandular; finely serrate. Petiole—medium length (8 to 11 mm.); moderately thick (about 2 mm.). Glands—average number—2 to 7; mostly opposite; medium size; reniform; red. Position—near the base of leaf on upper half of the petiole; also on base of leaf blade. Stipules—early deciduous; 4 to 6 mm. in length; narrow with pointed apex; with glandular teeth on the margins.

*Flowers.*—First bloom from February 27 to March 10. Full bloom from March 12 to March 20. Early compared with standard varieties; large; pink.

Fruit:

*Maturity when described.*—Firm ripe. Date—July 18, 1950.

*Size.*—Somewhat variable; large to medium size; with moderate thinning. Diameter axial—1¾ inches to 2¼ inches; transverse in suture plane—2 inches to 2¼ inches; at right angles to suture plane—1⅜ inches to 2¼ inches.

*Form.*—Somewhat variable; symmetrical; broadly ovoid. Suture—an inconspicuous line; extends from base to apex; has slight depression on all sides of pistil point.

Ventral surface — rounded slightly throughout both sides; lips—nearly equal. Stem cavity—rounded with suture showing on one side; depth—10 to 12 mm.; breadth—¾ inch; markings—suture more distinct in stem cavity. Base—rounded to truncate; a slight transverse depression caused by branch to which stem is joined. Apex—rounded; slightly depressed; pistil point in depression apical. Stem—length, ¼ inch; medium to stout; glabrous; adherence to stone—medium. Skin—thick to medium; tough to medium; somewhat tenacious to flesh; tendency to crack—none in wet or dry season. Color—on portions heavily shaded by leaves or branches near Barium Yellow, Plate 503, page 131, shaded with Cardinal Red, Plate 822, page 168, in less heavily shaded areas. Most of surface is between Cardinal Red, Plate 822, page 168, and Chrysanthemum Crimson, Plate 824/1, page 169, flecked and streaked lightly with Oxblood Red, Plate 00823, page 191. The darkest portions are near Dark Perilla Purple, Plate XXXVII (Ridgway). Down—none.

*Flesh.*—Color—near Chinese Yellow, Plate 606, page 68; Currant Red, Plate 821/2, page 167, entering the flesh from pit cavity to a depth of 3 to 5 mm.; surface of pit cavity—near Currant Red, Plate 821, page 167. Juice—abundant; rich; sweet. Texture—medium firm; medium fine. Fibres—few; tender. Ripens—evenly. Flavor—acid-sugar balance closely approaches ideal. Aroma — pronounced. Eating quality—best.

*Stone.*—Free. Fibres—short; retains short fibre-like threads along ridges. Size—medium; length—25 to 30 mm.; breadth—20 to 24 mm., at widest point. Thickness—

16 to 18 mm. Form—nearly ovoid, being slightly greater in breadth than in thickness. Base—nearly straight; hilum—narrowly oval; apex—cuspidate. Sides—equal; surface—irregularly furrowed near apex; pitted from base to above center. Ridges—usually rounded. Pits—some circular, most elongated; ventral edge—thick with slight wing toward base. Dorsal edge—medium, with shallow groove (2 to 3 mm.) from base to above center; ridges on either side—interrupted. Color—near Sayal Brown, Plate XXIX (Ridgway); inside of pits and furrows near Light Pinkish Cinnamon, Plate XXIX (Ridgway), stained with Currant Red, Plate 821/2, page 167, near base and along edges. Tendency to split—none.

Use: Market; local; dessert.

Keeping quality: Good.

Resistance to insects: Good to medium resistance to thrips, as determined by comparison with other varieties grown under comparable conditions at Ontario, California.

Shipping quality: Good.

I claim:

A new and distinct variety of nectarine plant of the yellow-fleshed, freestone type, characterized as to novelty by its resemblance to the variety "Pioneer" (Plant Patent No. 787), but dominantly distinguished therefrom by its shorter winter chilling requirement, by its earlier ripening period, by its more vigorous, larger and more obconic habit of growth, by its longer, more upright and slender lateral growths, and by the more orange coloring in the skin and lesser acidity of its fruit, substantially as shown and described herein.

HERBERT C. SWIM.

No references cited.